United States Patent
Rallapalli et al.

(10) Patent No.: US 11,225,449 B2
(45) Date of Patent: Jan. 18, 2022

(54) OPTIMIZATION OF 2-EH PRODUCT RECOVERY SYSTEM USING PROCESS INTENSIFICATION

(71) Applicant: SABIC Global Technologies B.V., Bergen op Zoom (NL)

(72) Inventors: Jagan Mohan Rallapalli, Riyadh (SA); Ameen Ghamdi-Al, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/054,435

(22) PCT Filed: Apr. 29, 2019

(86) PCT No.: PCT/IB2019/053505
§ 371 (c)(1),
(2) Date: Nov. 10, 2020

(87) PCT Pub. No.: WO2019/220249
PCT Pub. Date: Nov. 21, 2019

(65) Prior Publication Data
US 2021/0221759 A1    Jul. 22, 2021

Related U.S. Application Data

(60) Provisional application No. 62/671,929, filed on May 15, 2018.

(51) Int. Cl.
*C07C 29/84* (2006.01)
*C07C 29/80* (2006.01)

(52) U.S. Cl.
CPC ............. *C07C 29/84* (2013.01); *C07C 29/80* (2013.01)

(58) Field of Classification Search
CPC ...................................................... C07C 29/84
USPC ......................................................... 568/918
See application file for complete search history.

(56) References Cited

U.S. PATENT DOCUMENTS

| 3,232,998 A * | 2/1966 | Arthur ................... C07C 29/88 568/913 |
| 3,431,311 A | 3/1969 | Cooper et al. |
| 3,703,444 A | 11/1972 | Graefje |
| 5,865,957 A | 2/1999 | Ueda |

FOREIGN PATENT DOCUMENTS

| CN | 105237350 A | 1/2016 |
| CN | 205011671 U | 2/2016 |
| RU | 2312850 C1 | 12/2007 |

OTHER PUBLICATIONS

Comils et al. "Ethylhexanol Process." Encyclopedia of Chemical Processing and Design. Vol 20, Ethanol as fuel: Options, Advantages and Disadvantages to Exhaust Stacks, Cost. John J. McKetta & William A. Cunningham, Marcel Dekker, Inc., New York and Basel, 1984 (379-383), partial.
Garcia-Cabeza et al. "Allylic Oxidation of Alkenes Catalyzed by a Copper-Aluminum Mixed Oxide." Organic Letters, ACS Publications (2014) 16, 1598-1601, dx.doi.org/10.1021/ol500198c.
International Search Report and Written Opinion for PCT/IB2019/053505 dated Aug. 19, 2019, 9 pages.
Naqvi, Syed. "Oxo Alcohols." Process Economics Program Report No. 21E. Sep. 2010. 11 pages.

* cited by examiner

*Primary Examiner* — Ana Z Muresan
(74) *Attorney, Agent, or Firm* — Norton Rose Fulbright US LLP (57) ABSTRACT

Systems and methods of recovering 2-ethyl hexanol from crude alcohol are disclosed. The crude alcohol originates from a reactor that produces 2-ethyl hexanol and is first distilled in a first distillation column The distillate from the first distillation column is then further distilled in a second distillation column. A side stream is drawn from the second distillation column and recycled to the reactor that produces 2-ethyl hexanol. The bottom stream from the second distillation column is mixed with the bottom stream from the first distillation column. The combined stream is further distilled in a third distillation column to produce a 2-ethyl hexanol product stream.

20 Claims, 3 Drawing Sheets

Table 1. Streams and compositions for the second distillation column

| | Units | 408E-REF | 408OPIN | 408E-BOT | 454C-IN | Side Strm |
|---|---|---|---|---|---|---|
| - Mass Flows | kg/hr | 694.97 | 1717.18 | 500 | 1162.15 | 750 |
| H2 | kg/hr | 0 | 0 | 0 | 0 | 0 |
| N2 | kg/hr | 0.062776 | 0.211978 | 1.98699e-45 | 0.274754 | 1.39648e-11 |
| WATER | kg/hr | 2.61284 | 5.42148 | 1.30741e-21 | 8.03423 | 9.06104e-05 |
| N-BAL | kg/hr | 0 | 0 | 0 | 0 | 0 |
| BUTANOL | kg/hr | 328.447 | 219.734 | 1.18935e-09 | 547.433 | 0.74806 |
| EPA | kg/hr | 0 | 0 | 0 | 0 | 0 |
| EHA | kg/hr | 184.43 | 141.75 | 0.0112066 | 307.385 | 18.7833 |
| EMPOH | kg/hr | 11.0092 | 18.2684 | 1.52743 | 18.3479 | 9.40234 |
| 2-EH | kg/hr | 168.409 | 1331.8 | 498.461 | 280.677 | 721.066 |
| C16RESID | kg/hr | 0 | 0 | 0 | 0 | 0 |
| I-BAL | kg/hr | 0 | 0 | 0 | 0 | 0 |
| - Mass Fractions | | | | | | |
| H2 | | 0 | 0 | 0 | 0 | 0 |
| N2 | | 9.0329e-05 | 0.000123445 | 3.97399e-48 | 0.000236418 | 4.52864e-14 |
| WATER | | 0.00375965 | 0.0031572 | 2.61482e-24 | 0.00691324 | 1.20814e-07 |
| N-BAL | | 0 | 0 | 0 | 0 | 0 |
| BUTANOL | | 0.472605 | 0.127962 | 2.37871e-12 | 0.471051 | 0.000997414 |
| EPA | | 0 | 0 | 0 | 0 | 0 |
| EHA | | 0.265378 | 0.0825479 | 2.24133e-05 | 0.264497 | 0.0250444 |
| EMPOH | | 0.0158413 | 0.0106386 | 0.00305486 | 0.0157878 | 0.0125365 |
| 2-EH | | 0.242325 | 0.775571 | 0.996923 | 0.241515 | 0.961422 |
| C16RESID | | 0 | 0 | 0 | 0 | 0 |
| I-BAL | | 0 | 0 | 0 | 0 | 0 |

FIG. 3

OPTIMIZATION OF 2-EH PRODUCT RECOVERY SYSTEM USING PROCESS INTENSIFICATION

CROSS REFERENCE TO RELATED APPLICATIONS

This application is a national phase application under 35 U.S.C. § 371 of International Application No. PCT/IB2019/053505 filed Apr. 29, 2019, which claims priority to U.S. Provisional Patent Application No. 62/671,929 filed May 15, 2018. The entire contents of each of the above-referenced disclosures is specifically incorporated by reference herein without disclaimer.

FIELD OF INVENTION

The present invention generally relates to 2-ethyl hexanol production processes. More specifically, the present invention relates to a 2-ethyl hexanol production recovery process that utilizes multiple distillation columns to recover 2-ethyl hexanol from a crude alcohol.

BACKGROUND OF THE INVENTION 2-ethyl hexanol (2-EH) is primarily used as feedstock in the production of plasticizers and lubricants due to its viscosity reducing and freezing point lowering abilities. 2-ethyl hexanol can also be used as food flavor ingredient and/or fragrance ingredient. Moreover, 2-ethyl hexanol can be reacted with nitric acid to form an octane booster.

Generally, 2-ethyl hexanol is produced from synthesis gas (carbon monoxide and hydrogen) and propylene. In the process, n-butyraldehyde is formed via hydroformylation of propylene. The n-butyraldehyde is subsequently converted to 2-ethyl, 3-propyl acrolein (EPA) via simultaneous aldolisation and dehydration. Then, EPA is partially hydrogenated to form 2-ethyl hexanal (EHA), which is further hydrogenated to form 2-ethyl hexanol.

The produced 2-ethyl hexanol along with all the intermediate products, such as EPA, EHA, or other hydrocarbons, also known as crude alcohol, are separated to recover highly purified 2-ethyl hexanol. Conventionally, 2-ethyl hexanol is recovered from the crude alcohol using a series of distillation columns. However, the conventional purification process has relatively low energy efficiency and limited recovery efficiency of 2-ethyl hexanol, resulting in low overall 2-ethyl hexanol productivity and high production cost for 2-ethyl hexanol production plants.

Overall, while methods of recovering 2-ethyl hexanol exist, the need for improvements in this field persists in light of at least the aforementioned drawbacks.

BRIEF SUMMARY OF THE INVENTION

A solution to at least some of the above-mentioned problems associated with the production, especially the purification and recovery of 2-ethyl hexanol has been discovered. The solution resides in a 2-EH recovery process that recovers intermediate product and additional 2-EH from a distillate of crude alcohol. Notably, the method comprises distilling the crude alcohol to form a distillate stream and a bottom stream and further distilling the distillate stream in a second distillation column and the bottom stream in a third distillation column. The bottom stream from the second distillation column is further distilled in the third distillation column. This can be beneficial because a considerable amount of 2-EH from the bottom stream of the second distillation column is recovered with minimal added energy consumption. This leads to increased productivity of the 2-EH production method and reduced energy consumption per unit 2-EH produced in the method as compared with conventional methods. Therefore, the methods of the present invention provide a technical advantage over at least some of the problems associated with the currently available methods for producing 2-ethyl hexanol mentioned above.

Embodiments of the invention include a method of recovering 2-EH from crude alcohol. The method includes distilling, in a first distillation column, the crude alcohol to produce a first distillate comprising (1) light components having a lower boiling point than butanol, (2) butanol, (3) EHA, (4) EPA, (5) water, and (6) 2-EH. The method further includes distilling, in a second distillation column, the first distillate to produce a second distillate comprising butanol and water. The method further includes flowing a liquid side stream from the second distillation column, wherein the liquid side stream comprises EHA and 2-EH. The method further still includes recycling the liquid side stream to a reactor that produces the crude alcohol. The method further includes distilling, in a third distillation column, a bottom stream comprising 2-EH and heavy components that have a boiling point higher than 2-EH from the first distillation column to produce a third distillate comprising 2-EH.

Embodiments of the invention include a method of recovering 2-EH from crude alcohol. The method comprises distilling, in a first distillation column, the crude alcohol to produce a first distillate comprising (1) light components having a lower boiling point than butanol, (2) butanol, (3) EHA, (4) EPA, (5) water, and (6) 2-EH. The method further comprises distilling, in a second distillation column, the first distillate to produce a second distillate comprising butanol and water. The method further comprises flowing a liquid side stream from the second distillation column, wherein the liquid side stream comprises EHA and 2-EH. The method further includes recycling the liquid side stream to a reactor that produces the crude alcohol. The method further includes distilling, in a third distillation column, a bottom stream comprising 2-EH and heavy components that have a boiling point higher than 2-EH from the first distillation column to produce a third distillate comprising 2-EH. The method further still includes flowing a bottom stream comprising 2-EH and heavy components that have a boiling point higher than 2-EH from the second distillation column to the third distillation column.

Embodiments of the invention include a method of recovering 2-EH from crude alcohol. The method comprises distilling, in a first distillation column, the crude alcohol to produce a first distillate comprising (1) light components having a lower boiling point than butanol, (2) butanol, (3) EHA, (4) EPA, (5) water, and (6) 2-EH. The method further includes distilling, in a second distillation column, the first distillate to produce a second distillate comprising butanol and water. The method further includes flowing a liquid side stream from the second distillation column, wherein the liquid side stream comprises EHA and 2-EH. The method further includes recycling the liquid side stream a reactor that produces the crude alcohol. The method further still includes distilling, in a third distillation column, a bottom stream comprising 2-EH and heavy components that have a boiling point higher than 2-EH from the first distillation column to produce a third distillate comprising 2-EH. The method further includes flowing a bottom stream comprising 2-EH and heavy components that have a boiling point higher than 2-EH from the second distillation column to the third distillation column. The method further still includes distilling, in the third distillation column, the bottom stream comprising 2-EH and heavy components that have a boiling point higher than 2-EH from the second distillation column to produce additional 2-EH in the third distillate.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refers to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

Currently, crude alcohol that comprises 2-ethyl hexanol is produced from synthesis gas (carbon monoxide and hydrogen) and propylene. Conventional recovery processes have relatively low energy efficiency and limited recovery efficiency of 2-ethyl hexanol, resulting in high production costs and relatively low 2-ethyl hexanol productivity. The present invention provides a solution to these problems. The solution is premised on a method that includes using multiple distillation columns, where the influent and effluent streams of the distillation columns are combined and flowed amongst the distillation columns in an manner that maximizes the recovery of 2-ethyl hexanol. These and other non-limiting aspects of the present invention are discussed in further detail in the following sections.

A. System for Recovering 2-ethyl Hexanol

Figure 1:
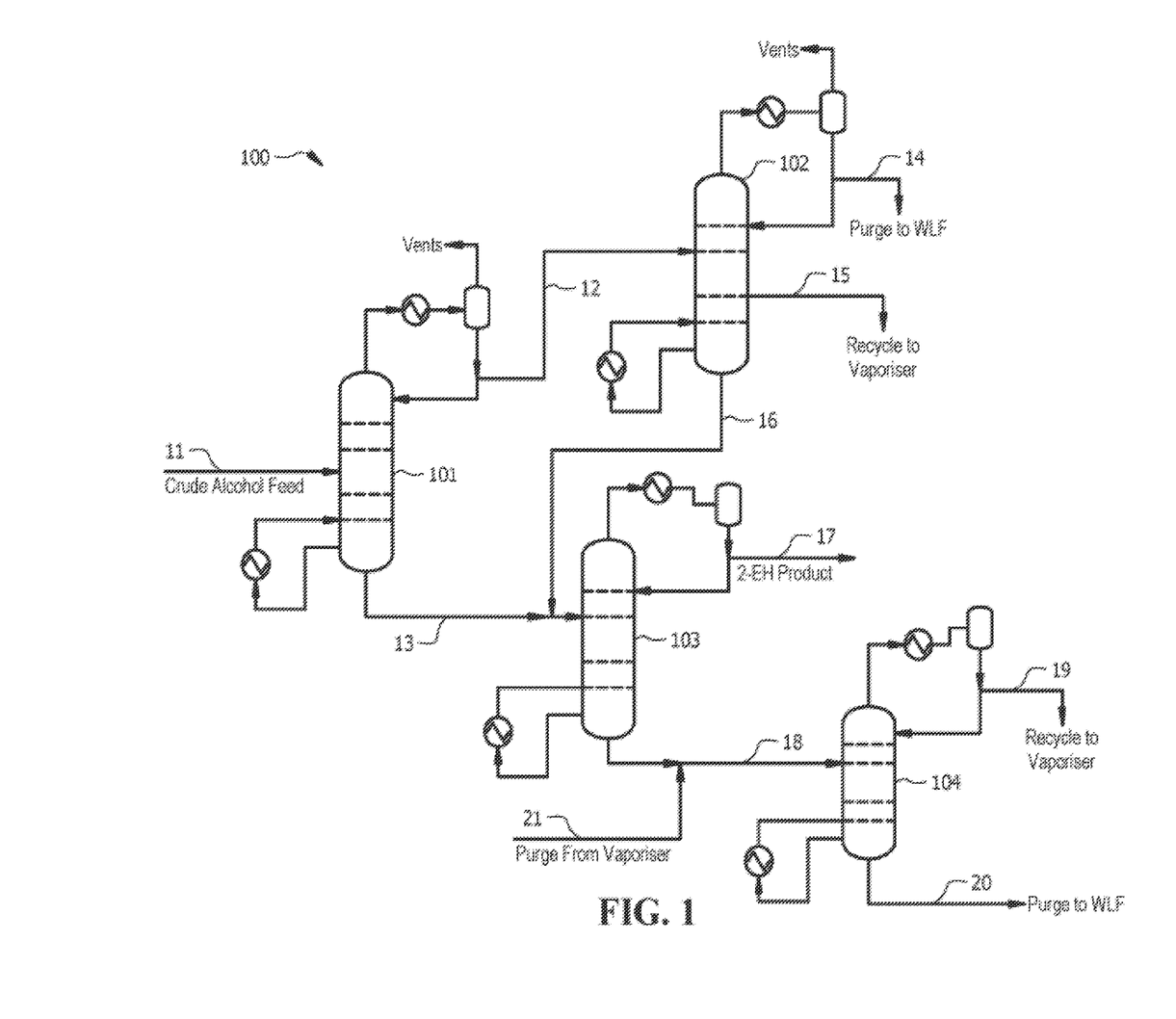
FIG. 1 shows a schematic diagram of a system of recovering 2-ethyl hexanol, according to embodiments of the invention.

In embodiments of the invention, the system for recovering 2-ethyl hexanol can include a plurality of integrated distillation columns. With reference to FIG. 1, a schematic diagram is shown of 2-EH recovering system 100 that is capable of recovering 2-EH from crude alcohol with higher 2-EH productivity and lower energy consumption per unit 2-EH compared to conventional 2-EH recovering systems.

According to embodiments of the invention, 2-EH recovering system 100 may include first distillation column 101 configured to receive and distill crude alcohol stream 11 to form first distillate stream 12 and first bottom stream 13. In embodiments of the invention, crude alcohol stream 11 may be from a 2-EH production reactor configured to react synthesis gas and propylene to produce the crude alcohol, which includes 2-EH.

In embodiments of the invention, an overhead outlet of first distillation column 101 may be in fluid communication with an inlet of second distillation column 102 such that first distillate stream 12 flows from first distillation column 101 to second distillation column 102. According to embodiments of the invention, second distillation column 102 may include an overhead outlet disposed on the top half of second distillation column 102. Second distillation column 102 may further include a middle outlet disposed at substantially middle section thereof. In embodiments of the invention, distillation column 102 may include 22 to 32 number of stages. The middle outlet of second distillation column 102 may be located at stage 10 in a 22 stage column to 15 stage in the 32 stage column.

In embodiments of the invention, distillation column 102 may further include a bottom outlet disposed at the bottom half thereof. In embodiments of the invention, second distillation column 102 may be configured to receive and distill first distillate stream 12 to form second distillate stream 14 flowing from the overhead outlet, liquid side stream 15 flowing from the middle outlet and second bottom stream 16 flowing from the bottom outlet of second distillation column 102.

In embodiments of the invention, a bottom outlet of first distillation column 101 may be in fluid communication with an inlet of third distillation column 103 such that first bottom stream 13 flows from first distillation column 101 to third distillation column In embodiments of the invention, third distillation column 103 may include an overhead outlet and a bottom outlet. In embodiments of the invention, the inlet of third distillation column 103 may be in fluid communication with the bottom outlet of second distillation column 102 such that second bottom stream 16 flows from second distillation column 102 to third distillation column 103. In embodiments of the invention, third distillation column 103 may be configured to receive and distill first bottom stream 13 and second bottom stream 16 to form third distillate stream 17 flowing from the overhead outlet thereof and third bottom stream 18 flowing from the bottom outlet thereof.

In embodiments of the invention, the bottom outlet of third distillation column 103 may be in fluid communication with an inlet of fourth distillation column 104 such that third bottom stream 18 flows from third distillation column 103 to fourth distillation column 104. In embodiments of the invention, fourth distillation column 104 may be configured to receive and distill third bottom stream 18 to form fourth distillate stream 19 and fourth bottom stream 20.

In embodiments of the invention, 2-EH recovering system 100 may further include a vaporizer (not shown). According to embodiments of the invention, the vaporizer may be in fluid communication with the middle outlet of second distillation column 102 such that liquid side stream 15 flows from second distillation column 102 to the vaporizer. In embodiments of the invention, the vaporizer may be further in fluid communication with an overhead outlet of fourth distillation column 104 such that fourth distillate stream 19 flows from fourth distillation column 104 to the vaporizer. According to embodiments of the invention, the vaporizer is configured to vaporize side stream 15 and/or fourth distillate stream 19. In embodiments of the invention, the vaporizer may be in fluid communication with a reactor that produces the crude alcohol comprising 2-ethyl hexanol. In embodiments of the invention, the vaporizer may be further in fluid communication with the inlet of fourth distillation column 104 such that purge stream 21 from the vaporizer is distilled in fourth distillation column 104.

B. Method for Recovering 2-ethyl Hexanol

Figure 2:
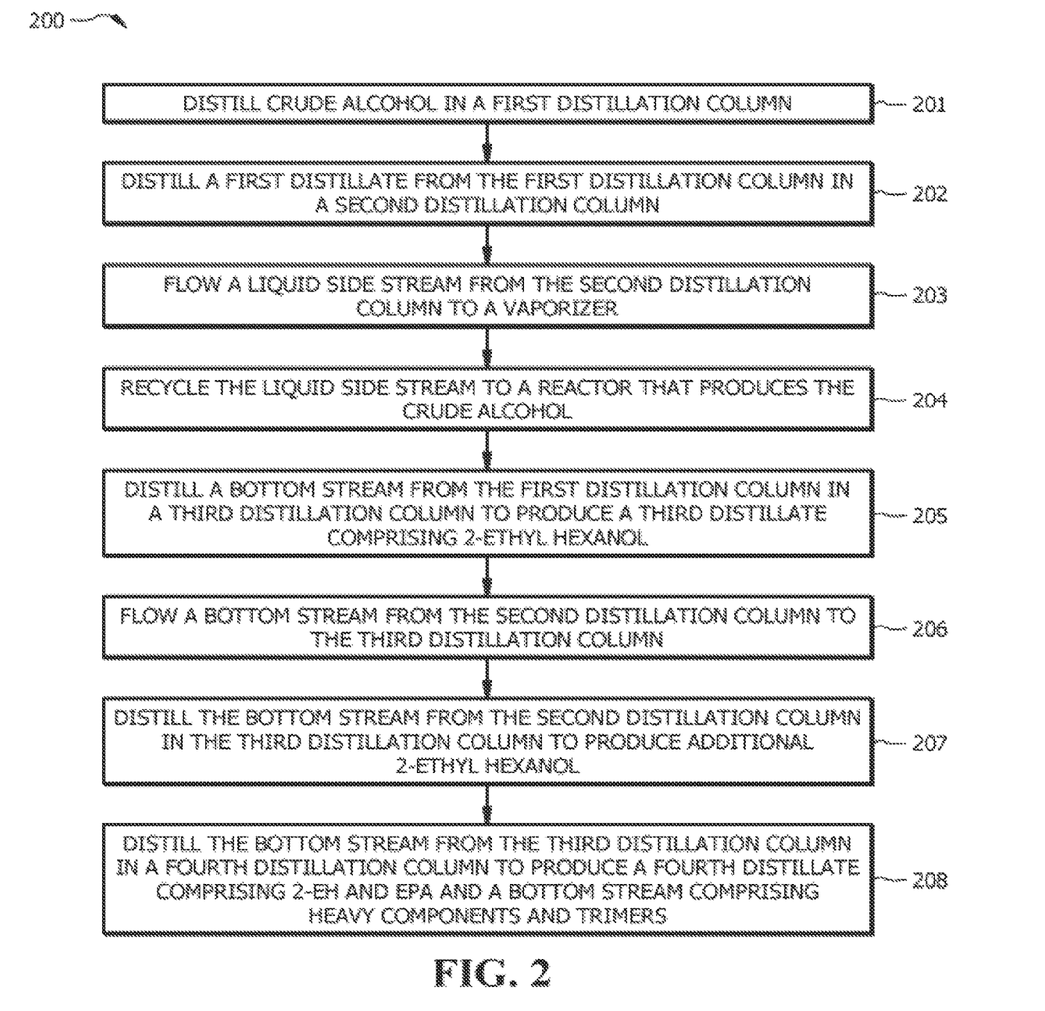
FIG. 2 shows a schematic flowchart of a method of recovering 2-ethyl hexanol, according to embodiments of the invention.

A method of recovering 2-ethyl hexanol from a crude alcohol is discovered to lower the production cost and increase the productivity of 2-ethyl hexanol as compared to conventional methods. As shown in FIG. 2, embodiments of the invention include method 200 for recovering 2-ethyl hexanol from a crude alcohol. Method 200 may be implemented by 2-EH recovering system 100, as shown in FIG. 1. According to embodiments of the invention, the crude alcohol may include 94 to 97 wt. % 2-ethyl hexanol and all ranges and values there between including 94 to 94.2 wt. %, 94.2 to 94.4 wt. %, 94.4 to 94.6 wt. %, 94.6 to 94.8 wt. %, 94.8 to 95.0 wt. %, 95.0 to 95.2 wt. %, 95.2 to 95.4 wt. %, 95.4 to 95.6 wt. %, 95.6 to 95.8 wt. %, 95.8 to 96.0 wt. %, 96.0 to 96.2 wt. %, 96.2 to 96.4 wt. %, 96.4 to 96.6 wt. %, 96.6 to 96.8 wt. %, and 96.8 to 97.0 wt. %. In embodiments of the invention, the crude alcohol may further include 0.4 to 1.0 wt. % 2-ethyl hexanal (EHA), 0.001 to 0.002 wt. % 2-ethyl, 3-propyl acrolein (EPA), 1 to 2 wt. % butanol, 0.5 to 1.0 wt. % heavy hydrocarbons, and 0.6 to 1.0 wt. % water.

In embodiments of the invention, the crude alcohol is produced from synthesis gas and propylene.

According to embodiments of the invention, as shown in block 201, method 200 may include distilling, in first distillation column 101, the crude alcohol of crude alcohol stream 11 to produce a first distillate comprising light components having a lower boiling point than butanol, EHA, EPA, water, and 2-EH. In embodiments of the invention, the distilling in block 201 further produces first bottom stream 13 comprising primarily 2-ethyl hexanol flowing from the bottom outlet of first distillation column 101. In embodiments of the invention, the first distillate (of first distillate stream 12) may flow from the overhead outlet of first distillation column 101 to second distillation column 102. In embodiments of the invention, an operating temperature of first distillation column 101 at block 201 may be in a range of 148 to 155° C. and all ranges and values there between including 148.0 to 148.5° C., 148.5 to 149.0° C., 149.0 to 149.5° C., 149.5 to 150.0° C., 150.0 to 150.5° C., 150.5 to 151.0° C., 151.0 to 151.5° C., 151.5 to 152.0° C., 152.0 to 152.5° C., 152.5 to 153.0° C., 153.0 to 153.5° C., 153.5 to 154.0° C., 154.0 to 154.5° C., and 154.5 to 155.0° C. An operating pressure of first distillation column 101 at block 201 may be in a range of 0.2 to 0.4 bar and all ranges and values there between including 0.2 to 0.22 bar, 0.22 to 0.24 bar, 0.24 to 0.26 bar, 0.26 to 0.28 bar, 0.28 to 0.30 bar, 0.30 to 0.32 bar, 0.32 to 0.34 bar, 0.34 to 0.36 bar, 0.36 to 0.38 bar, and 0.38 to 0.40 bar.

In embodiments of the invention, as shown in block 202, method 200 may include distilling, in second distillation column 102, the first distillate (first distillate stream 12) to produce a second distillate (second distillate stream 14). In embodiments of the invention, the second distillate may include butanol and water. The second distillate may be used as waste liquid fuel (WLF). According to embodiments of the invention, as shown in block 203, method 200 may further include flowing liquid side stream 15 from second distillation column 102 to the vaporizer. In embodiments of the invention, second distillation column 102 may include 22 to 32 actual number of stages. Liquid side stream may be drawn from stage 10 to stage 15 of second distillation column 102. In embodiments of the invention, an operating temperature of second distillation column 102 at block 202 may be in a range of 140 to 148° C. and all ranges and values there between including 140 to 140.5° C., 140.5 to 141.0° C., 141.0 to 141.5° C., 141.5 to 142.0° C., 142.0 to 142.5° C., 142.5 to 143.0° C., 143.0 to 143.5° C., 143.5 to 144.0° C., 144.0 to 144.5° C., 144.5 to 145.0° C., 145.0 to 145.5° C., 145.5 to 146.0° C., 146.0 to 146.5° C., 146.5 to 147.0° C., 147.0 to 147.5° C., and 147.5 to 148.0° C. An operating pressure of second distillation column 102 at block 202 may be in a range of 0.4 to 0.6 bar and all ranges and values there between including 0.40 to 0.42 bar, 0.42 to 0.44 bar, 0.44 to 0.46 bar, 0.46 to 0.48 bar, 0.48 to 0.50 bar, 0.50 to 0.52 bar, 0.52 to 0.54 bar, 0.54 to 0.56 bar, 0.56 to 0.58 bar, and 0.58 to 0.60 bar.

In embodiments of the invention, liquid side stream 15 may include primarily EHA and 2-EH. In embodiments of the invention, liquid side stream 15 may include 2.5 to 5.0 wt. % EHA and all ranges and values there between including ranges of 2.5 to 2.6 wt. %, 2.6 to 2.7 wt. %, 2.7 to 2.8 wt. %, 2.8 to 2.9 wt. %, 2.9 to 3.0 wt. %, 3.0 to 3.1 wt. %, 3.1 to 3.2 wt. %, 3.2 to 3.3 wt. %, 3.3 to 3.4 wt. %, 3.4 to 3.5 wt. %, 3.5 to 3.6 wt. %, 3.6 to 3.7 wt. %, 3.7 to 3.8 wt. %, 3.8 to 3.9 wt. %, 3.9 to 4.0 wt. %, 4.0 to 4.1 wt. %, 4.1 to 4.2 wt. %, 4.2 to 4.3 wt. %, 4.3 to 4.4 wt. %, 4.4 to 4.5 wt. %, 4.5 to 4.6 wt. %, 4.6 to 4.7 wt. %, 4.7 to 4.8 wt. %, 4.8 to 4.9 wt. %, and 4.9 to 5.0 wt. %.

In embodiments of the invention, liquid side stream 15 may include 95 to 97.5 wt. % 2-ethyl hexanol and all ranges and values there between, including ranges of 95.0 to 95.1 wt. %, 95.1 to 95.2 wt. %, 95.2 to 95.3 wt. %, 95.3 to 95.4 wt. %, 95.4 to 95.5 wt. %, 95.5 to 95.6 wt. %, 95.6 to 95.7 wt. %, 95.7 to 95.8 wt. %, 95.8 to 95.9 wt. %, 95.9 to 96.0 wt. %, 96.0 to 96.1 wt. %, 96.1 to 96.2 wt. %, 96.2 to 96.3 wt. %, 96.3 to 96.4 wt. %, 96.4 to 96.5 wt. %, 96.5 to 96.6 wt. %, 96.6 to 96.7 wt. %, 96.7 to 96.8 wt. %, 96.8 to 96.9 wt. %, 96.9 to 97.0 wt. %, 97.0 to 97.1 wt. %, 97.1 to 97.2 wt. %, 97.2 to 97.3 wt. %, 97.3 to 97.4 wt. %, and 97.4 to 97.5 wt. %.

In embodiments of the invention, liquid side stream may be vaporized. As shown in block 204, method 200 may include recycling liquid side stream 15 to a reactor that produces the crude alcohol. In embodiments of the invention, recycling at block 204 further includes producing 2-ethyl hexanol using EHA from liquid side stream 15. In embodiments of the invention, as shown in block 205, method 200 may include distilling, in third distillation column 103, first bottom stream 13 comprising 2-ethyl hexanol and heavy components that have a boiling point higher than 2-ethyl hexanol from first distillation column 101 to produce third distillate stream 17 comprising 2-ethyl hexanol. In embodiments of the invention, first bottom stream 13 may include 98 to 99 wt. % 2-ethyl hexanol and all ranges and values there between including 98.1 wt. %, 98.2 wt. %, 98.3 wt. %, 98.4 wt. %, 98.5 wt. %, 98.6 wt. %, 98.7 wt. %, 98.8 wt. %, and 98.9 wt. %. In embodiments of the invention, the heavy components in first bottom stream 13 may include 4-Methyl pentanol (EMPOH), 2-Ethylhexanoic acid (C16H3202), 2-Ethylhexyl butyrate (C12H2402), or combinations thereof. In embodiments of the invention, an operating temperature of third distillation column 103 may be in a range of 120 to 130° C. and all ranges and values there between including 120 to 120.5° C., 120.5 to 121° C., 121 to 121.5° C., 121.5 to 122° C., 122 to 122.5° C., 122.5 to 123° C., 123 to 123.5° C., 123.5 to 124° C., 124 to 124.5° C., 124.5 to 125° C., 125 to 125.5° C., 125.5 to 126° C., 126 to 126.5° C., 126.5 to 127° C., 127 to 127.5° C., 127.5 to 128° C., 128 to 128.5° C., 128.5 to 129° C., 129 to 129.5° C., and 129.5 to 130° C. An operating pressure of third distillation column 103 may be in a range of 0.1 to 0.2 bar and all ranges and values there between including 0.11 bar, 0.12 bar, 0.13 bar, 0.14 bar, 0.15 bar, 0.16 bar, 0.17 bar, 0.18 bar, and 0.19 bar.

According to embodiments of the invention, as shown in block 206, method 200 may further include flowing second bottom stream 16 comprising 2-ethyl hexanol and heavy components that have a boiling point higher than 2-ethyl hexanol from second distillation column 102 to third distillation column 103. In embodiments of the invention, second bottom stream 16 may include 98.0 to 99.8 wt. % 2-ethyl hexanol and all ranges and values there between including ranges of 98.0 to 98.1 wt. %, 98.1 to 98.2 wt. %, 98.2 to 98.3 wt. %, 98.3 to 98.4 wt. %, 98.4 to 98.5 wt. %, 98.5 to 98.6 wt. %, 98.6 to 98.7 wt. %, 98.7 to 98.8 wt. %, 98.8 to 98.9 wt. %, 98.9 to 99.0 wt. %, 99.0 to 99.1 wt. %, 99.1 to 99.2 wt. %, 99.2 to 99.3 wt. %, 99.3 to 99.4 wt. %, 99.4 to 99.5 wt. %, 99.5 to 99.6 wt. %, 99.6 to 99.7 wt. %, and 99.7 to 99.8 wt. %. In embodiments of the invention, the heavy components in second bottom stream 16 may include EMPOH, Trimethyl heptadiene-2-one, Ethyl trimethyl pentonate, or combinations thereof. In embodiments of the invention, second bottom stream 16 may be combined with first bottom stream 13.

According to embodiments of the invention, as shown in block 207, method 200 may further include distilling, in third distillation column 103, second bottom stream 16 from second distillation column 102 comprising 2-ethyl hexanol and heavy components that have a boiling point higher than 2-ethyl hexanol to produce additional 2-ethyl hexanol in third distillate stream 17. In embodiments of the invention, third distillate stream 17 may include 99.5 to 99.7 wt. % 2-ethyl hexanol and all ranges and values there between, including ranges of 99.50 to 99.52 wt. %, 99.52 to 99.54 wt. %, 99.54 to 99.56 wt. %, 99.56 to 99.58 wt. %, 99.58 to 99.60 wt. %, 99.60 to 99.62 wt. %, 99.62 to 99.64 wt. %, 99.64 to 99.66 wt. %, 99.66 to 99.68 wt. %, and 99.68 to 99.70 wt. %. In embodiments of the invention, third distillate stream 17 is the product stream for 2-ethyl hexanol recovery system 100.

In embodiments of the invention, as shown in block 208, method 200 may further include distilling, in fourth distillation column 104, third bottom stream 18 from third distillation column 103 comprising EPA and 2-ethyl hexanol to produce the fourth distillate of fourth distillate stream 19 comprising 2-ethyl hexanol and EPA and fourth bottom stream 20 comprising trimers and heavy components. In embodiments of the invention, third bottom stream 18 may include 5 to 10 wt. % 2-ethyl hexanol and all ranges and values there between including 5.0 to 5.5 wt. %, 5.5 to 6.0 wt. %, 6.0 to 6.5 wt. %, 6.5 to 7.0 wt. %, 7.0 to 7.5 wt. %, 7.5 to 8.0 wt. %, 8.0 to 8.5 wt. %, 8.5 to 9.0 wt. %, 9.0 to 9.5 wt. %, and 9.5 to 10.0 wt. %. According to embodiments of the invention, third bottom stream 18 may be merged with purge stream 21 from the vaporizer. Purge stream 21 may include EPA, 2-EH, 2-Ethylhexyl butyrate, or combinations thereof.

In embodiments of the invention, fourth distillate stream 19 may include 7 to 15 wt. % EPA and 85 to 93 wt. % 2-ethyl hexanol. In embodiments of the invention, fourth distillate stream 19 may be flowed to the vaporizer and recycled to the reactor that produces the crude alcohol. Fourth bottom stream 20 may be purged as waste liquid fuel (WLF). According to embodiments of the invention, an operating temperature of fourth distillation column 104 at block 208 may be in a range of 130 to 140° C. and all ranges and values there between, including 131° C., 132° C., 133° C., 134° C., 135° C., 136° C., 137° C., 138° C., and 139° C. An operating pressure of fourth distillation column 104 at block 208 may be in a range of 0.15 to 0.3 bar and all ranges and values there between including ranges of 0.15 to 0.16 bar, 0.16 to 0.17 bar, 0.17 to 0.18 bar, 0.18 to 0.19 bar, 0.19 to 0.20 bar, 0.20 to 0.21 bar, 0.21 to 0.22 bar, 0.22 to 0.23 bar, 0.23 to 0.24 bar, 0.24 to 0.25 bar, 0.25 to 0.26 bar, 0.26 to 0.27 bar, 0.27 to 0.28 bar, 0.28 to 0.29 bar, and 0.29 to 0.30 bar.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

As part of the disclosure of the present invention, a specific example is included below. The example is for illustrative purposes only and is not intended to limit the invention. Those of ordinary skill in the art will readily recognize parameters that can be changed or modified to yield essentially the same results.

Example

Simulation of a 2-EH Production Process

Simulations were run in Aspen® Plus platform for a 2-EH production process according to embodiments of the invention. The simulation model was validated. In the simulation runs, the operating condition for the second distillation column (column 102) included an operation temperature at 142° C. and an operating pressure of 0.48 bar.

Figure 3:
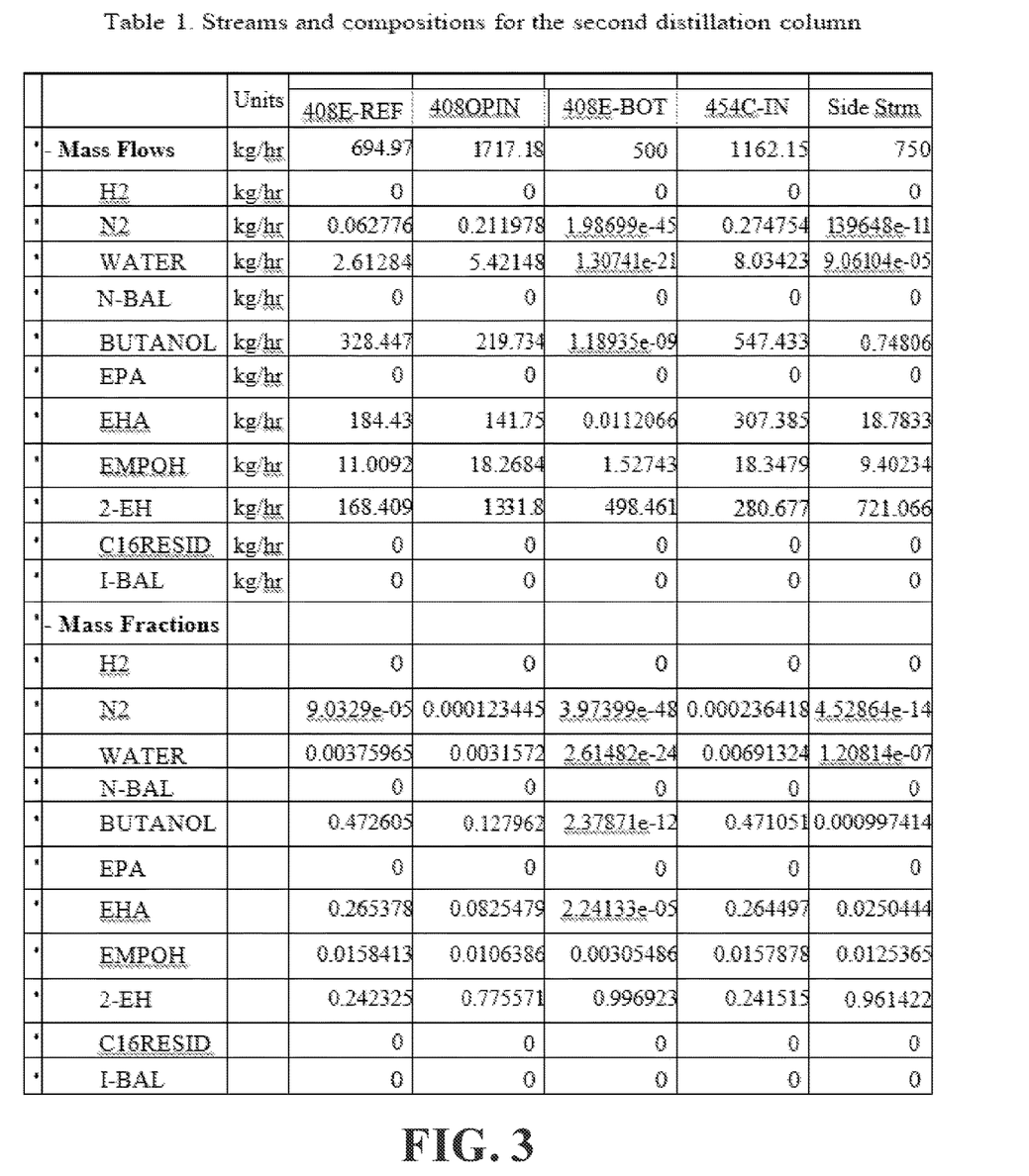
FIG. 3 shows a table with the mass flows and compositions for streams flowing in and out of a distillation column as described in the Examples section below.

Mass flows and compositions for streams flowing in and out of column 102 (as shown in FIG. 1) were calculated. The results are shown in Table 1. In Table 1, stream 408E-REF is the liquid reflux stream (stream flowing from the condenser back to the distillation column) of column 102 (FIG. 1). Stream 4080PIN is the feed stream of column 102 (first distillate stream 12). Stream 408E-BOT is the bottom stream of column 102 (second bottom stream 16). Stream 454-IN is the overhead stream from column 102 to the condenser. Side stream is liquid side stream 15 as shown in FIG. 1.

JAs shown in Table 1, stream 408E-BOT (second bottom stream 16), which was routed to third distillation column 103, has a mass flow rate of 500 kg per hour. 2-EH composition in stream 408E-BOT was about 99.7 wt. %. Therefore, considerably more 2-EH was recovered in the process with minimum increase of energy compared to the conventional process, which recycles stream 408E-BOT (second bottom stream 16) back to the reactor for producing 2-EH.

In the context of the present invention, embodiments 1-15 are described. Embodiment 1 is a method of recovering 2-EH from crude alcohol. The method includes 10 distilling, in a first distillation column, the crude alcohol to produce a first distillate including (1) light components having a lower boiling point than butanol, (2) butanol, (3) EHA, (4) EPA, (5) water, and (6) 2-EH, then distilling, in a second distillation column, the first distillate to produce a second distillate comprising butanol and water, flowing a liquid side stream from the second distillation column, wherein the liquid side stream includes EHA and 2-EH, recycling the liquid side stream to a reactor that produces the crude alcohol, and distilling, in a third distillation column, a bottom stream comprising 2-EH and heavy components that have a boiling point higher than 2-EH from the first distillation column to produce a third distillate comprising 2-EH. Embodiment 2 is the method of embodiment 1, further including flowing a bottom stream comprising 2-EH and heavy components that have a boiling point higher than 2-EH from the second distillation column to the third distillation column. Embodiment 3 is the method of embodiment 2, further including distilling, in the third distillation column, the bottom stream from the second distillation column including 2-EH and heavy components that have a boiling point higher than 2-EH to produce additional 2-EH in the third distillate. Embodiment 4 is the method of embodiment 3, further including distilling, in a fourth distillation column, a bottom stream from the third distillation column including EPA and 2-EH to produce a fourth distillate including 2-EH and EPA and a bottom stream from the fourth distillation column including trimers, and heavy components. Embodiment 5 is the method of embodiment 4, wherein the fourth distillate is recycled back to the reactor that produces the crude alcohol. Embodiment 6 is the method of either of embodiments 3 or 4, wherein the bottom stream from the fourth distillation column is purged as waste liquid fuel. Embodiment 7 is the method of any of embodiments 3 to 6, wherein the liquid side stream and the fourth distillate are vaporized before being flowed to the reactor that produced the crude alcohol. Embodiment 8 is the method of any of embodiments 1 to 7, wherein the crude alcohol is produced from propylene, carbon monoxide and hydrogen. Embodiment 9 is the method of any of embodiments 1 to 8, wherein the crude alcohol includes (1) primarily 2-EH, (2) 2-ethyl, 3-propyl acrolein (EPA), and (3) 2-ethyl hexanal (EHA). Embodiment 10 is the method of any of embodiments 1 to 9, wherein the liquid side stream includes 2.5% to 5.0% EHA and 95% to 97.5% 2-EH. Embodiment 11 is the method of any of embodiments 1 to 10, wherein the bottom stream from the second distillation column includes 99% to 99.6% 2-EH. Embodiment 12 is the method of any of claims 1 to 11, wherein the third distillate from the third distillation column includes 99.6% to 99.9% 2-EH. Embodiment 13 is the method of any of embodiments 1 to 12, wherein the second distillation column has an operating pressure of 0.4 to 0.6 bar. Embodiment 14 is the method of any of embodiments 1 to 13, wherein the second distillation column has an operating temperature of 140 to 148° C.

Embodiment 15 is a method of recovering 2-EH from crude alcohol. The method includes distilling, in a first distillation column, the crude alcohol to produce a first distillate including (1) light components having a lower boiling point than butanol, (2) butanol, (3) EHA, (4) EPA, (5) water, and (6) 2-EH, then distilling, in a second distillation column, the first distillate to produce a second distillate including butanol and water, flowing a liquid side stream from the second distillation column, wherein the liquid side stream includes EHA and 2-EH, recycling the liquid side stream a reactor that produces the crude alcohol, and distilling, in a third distillation column, a bottom stream including 2-EH and heavy components that have a boiling point higher than 2-EH from the first distillation column to produce a third distillate comprising 2-EH. The method further includes flowing a bottom stream including 2-EH and heavy components that have a boiling point higher than 2-EH from the second distillation column to the third distillation column, and distilling, in the third distillation column, the bottom stream including 2-EH and heavy components that have a boiling point higher than 2-EH from the second distillation column to produce additional 2-EH in the third distillate.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of recovering 2-ethyl hexanol from crude alcohol, the method comprising:
   distilling, in a first distillation column, the crude alcohol to produce a first bottom stream and a first distillate comprising (1) light components having a lower boiling point than butanol, (2) butanol, (3) 2-ethylhexanal, (4) 2-ethyl,3-propyl acrolein, (5) water, and (6) 2-ethyl hexanol;
   distilling, in a second distillation column, the first distillate to produce a second distillate comprising butanol and water, a liquid side stream and a second bottom stream;
   flowing the liquid side stream from a middle outlet of the second distillation column, wherein the liquid side stream comprises 2-ethylhexanal and 22-ethyl hexanol;
   recycling the liquid side stream to a reactor that produces the crude alcohol; and
   distilling, in a third distillation column, a bottom stream comprising 2-ethyl hexanol and heavy components that have a boiling point higher than 2-ethyl hexanol from the first distillation column to produce a third distillate comprising 2-ethyl hexanol;
   wherein the second distillation column has an operating temperature of 140 to 148° C.

2. The method of claim 1, further comprising flowing to the third column the second bottom stream, wherein the second bottom stream comprises 2-ethyl hexanol and heavy components that have a boiling point higher than 2-ethyl hexanol.

3. The method of claim 2, further comprising distilling, in the third distillation column, the second bottom stream from the second distillation column comprising 2-ethyl hexanol and heavy components that have a boiling point higher than 2-ethyl hexanol to produce additional 2-ethyl hexanol in the third distillate.

4. The method of claim 3, further comprising distilling, in a fourth distillation column, a third bottom stream from the third distillation column including 2-ethyl,3-propyl acrolein and 2-ethyl hexanol to produce a fourth distillate comprising 2-ethyl hexanol and 2-ethyl,3-propyl acrolein and a fourth bottom stream from the fourth distillation column comprising trimers, and heavy components.

5. The method of claim 4, wherein the fourth distillate is recycled back to the reactor that produces the crude alcohol.

6. The method of claim 3, wherein the fourth bottom stream from the fourth distillation column is purged as waste liquid fuel.

7. The method of claim 3, wherein the liquid side stream and the fourth distillate are vaporized before being flowed to the reactor that produced the crude alcohol.

8. The method of claim 1, wherein the crude alcohol is produced from propylene, carbon monoxide and hydrogen.

9. The method of claim 1, wherein the crude alcohol comprises (1) primarily 2-ethyl hexanol, (2) 2-ethyl, 3-propyl acrolein and (3) 2-ethyl hexanal.

10. The method of claim 1, wherein the liquid side stream comprises 2.5% to 5.0% 2-ethylhexanal and 95% to 97.5% 2-ethyl hexanol.

11. The method of claim 1, wherein the bottom stream from the second distillation column comprises 99% to 99.6% 2-ethyl hexanol.

12. The method of claim 1, wherein the third distillate from the third distillation column comprises 99.6% to 99.9% 2-ethyl hexanol; and wherein a third bottom stream from the third distillation column is merged with a purge stream from a vaporizer to produce a merged stream, and flowing the merged stream to a fourth distillation column;
   wherein the purge stream comprises at least one member selected from the group consisting of 2-ethyl hexanol, 2-ethyl,3-propyl acrolein and 2-Ethylhexyl butyrate, or combinations thereof.

13. The method of claim 1, wherein the second distillation column has an operating pressure of 0.4 to 0.6 bar.

14. The method of claim 1, wherein the second distillation column has an operating temperature of 148° C.

15. A method of recovering 2-ethyl hexanol from crude alcohol, the method comprising:
   distilling, in a first distillation column, the crude alcohol to produce a first bottom stream and a first distillate comprising (1) light components having a lower boiling point than butanol, (2) butanol, (3) 2-ethylhexanal, (4) 2-ethyl,3-propyl acrolein, (5) water, and (6) 2-ethyl hexanol;
   distilling, in a second distillation column, the first distillate to produce a second distillate stream comprising butanol and water, a liquid side stream and a second bottom stream;
   flowing the liquid side stream from a middle outlet of the second distillation column, wherein the liquid side stream comprises 2-ethylhexanal and 2-ethyl hexanol;
   recycling the liquid side stream a reactor that produces the crude alcohol; and
   distilling, in a third distillation column, third bottom stream comprising 2-ethyl hexanol and heavy components that have a boiling point higher than 2-ethyl hexanol from the first distillation column to produce a third distillate comprising 2-ethyl hexanol;
   flowing a bottom stream comprising 2-ethyl hexanol and heavy components that have a boiling point higher than 2-ethyl hexanol from the second distillation column to the third distillation column; and
   distilling, in the third distillation column, the bottom stream comprising 2-ethyl hexanol and heavy components that have a boiling point higher than 2-ethyl hexanol from the second distillation column to produce additional 2-ethyl hexanol in the third distillate;
   wherein the second distillation column has an operating temperature of 140 to 148° C.

16. The method of claim 2, wherein the second distillation column has an operating temperature of 140° C.

17. The method of claim 3, wherein the second distillation column has an operating temperature of 148° C.

18. The method of claim 4, wherein the second distillation column has an operating temperature of 148° C.

19. The method of claim 2, wherein the second distillation column has an operating pressure of 0.4 to 0.6 bar.

20. The method of claim 3, wherein the second distillation column has an operating pressure of 0.4 to 0.6 bar.

* * * * *

UNITED STATES PATENT AND TRADEMARK OFFICE
CERTIFICATE OF CORRECTION

PATENT NO. : 11,225,449 B2
APPLICATION NO. : 17/054435
DATED : January 18, 2022
INVENTOR(S) : Jagan Mohan Rallapalli et al.

It is certified that error appears in the above-identified patent and that said Letters Patent is hereby corrected as shown below:

In the Claims

At Column 11, Claim number 1, Line number 17, delete "22-ethyl hexanol" and replace with --2-ethyl hexanol--.
At Column 11, Claim number 9, Line number 57, add --,-- after "acrolein".

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*